US00PP35267P2

(12) United States Plant Patent
Olesen

(10) Patent No.: US PP35,267 P2
(45) Date of Patent: Jul. 18, 2023

(54) ROSE PLANT NAMED 'POULPA1096'

(50) Latin Name: *Rosa hybrida*
Varietal Denomination: Poulpa1096

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/803,613

(22) Filed: Sep. 13, 2022

(30) Foreign Application Priority Data

Sep. 24, 2021 (QZ) ..... PBR 2021/2360

(51) Int. Cl.
*A01H 5/02* (2018.01)
*A01H 6/74* (2018.01)

(52) U.S. Cl.
USPC ..... Plt./144
CPC ..... *A01H 6/749* (2018.05)

(58) Field of Classification Search
USPC ..... Plt./144
CPC ..... A01H 6/749; A01H 5/02
See application file for complete search history.

*Primary Examiner* — Keith O. Robinson

(57) ABSTRACT

A new garden rose plant of the Compact Floribunda class which has abundant, near white flowers and attractive foliage. This new and distinct variety has shown to be uniform and stable in the resulting generations from asexual propagation.

2 Drawing Sheets

Botanical designation: *Rosa hybrida.*

Variety denomination: 'Poulpa1096'.

This application claims priority to Plant Breeder's Rights Application Number 2021/2360, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulpa1096', originated as a single seedling from the stated cross.

The new variety may be distinguished from its male pollen parent and female seed parent primarily by the following characteristics. The male pollen parent plant has pure white flowers while the new variety has near white flowers. The female seed parent plant has flowers with a diameter of 60 mm while the new variety has a flower diameter of 85 mm.

The objective of the hybridization of this rose variety was to create a new and distinct variety with unique qualities, such as:

1. Uniform and abundant near white flowers;
2. Vigorous, but compact growth when propagated on its own roots;
3. Exceptional disease resistance.

This combination of qualities is not present in previously available commercial cultivars of this type, known to the inventor, and distinguish 'Poulpa1096' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulpa1096' was selected in the spring of 2014 by the inventor as a single plant from the progeny of the aforementioned hybridization.

Asexual reproduction of 'Poulpa1096' by rooted cuttings was first done by Mogens N. Olesen in the nursery in Fredensborg, Denmark in July, 2014. This initial and other subsequent asexual propagations conducted in controlled environments have demonstrated that the characteristics of 'Poulpa1096' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpa1096'.

Specifically illustrated in FIG. 1 of the drawings are open flowers viewed from above, flower petals and sepals detached revealing reproductive flower parts and receptacle.

Figure 1:
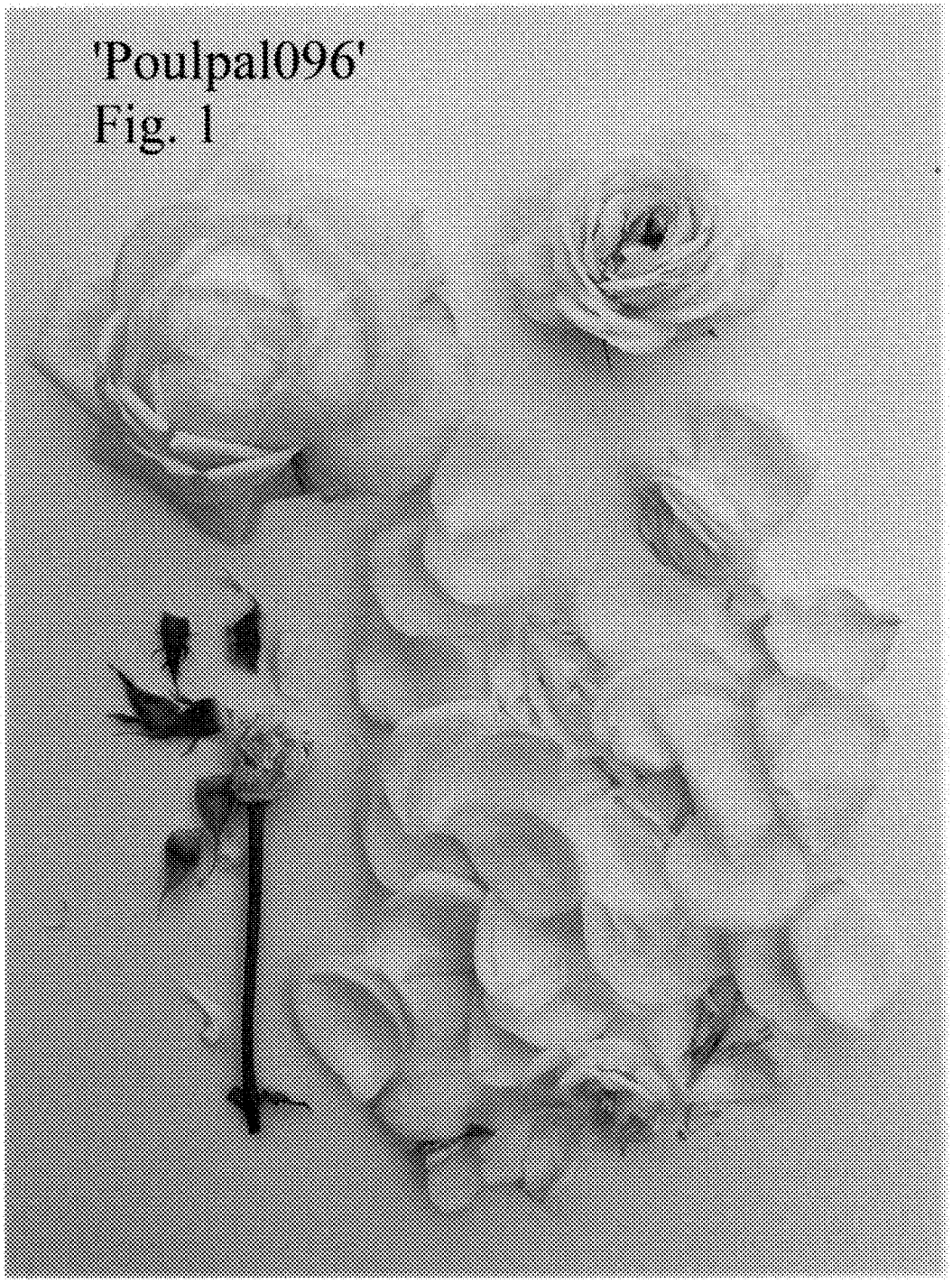
Figure 2:
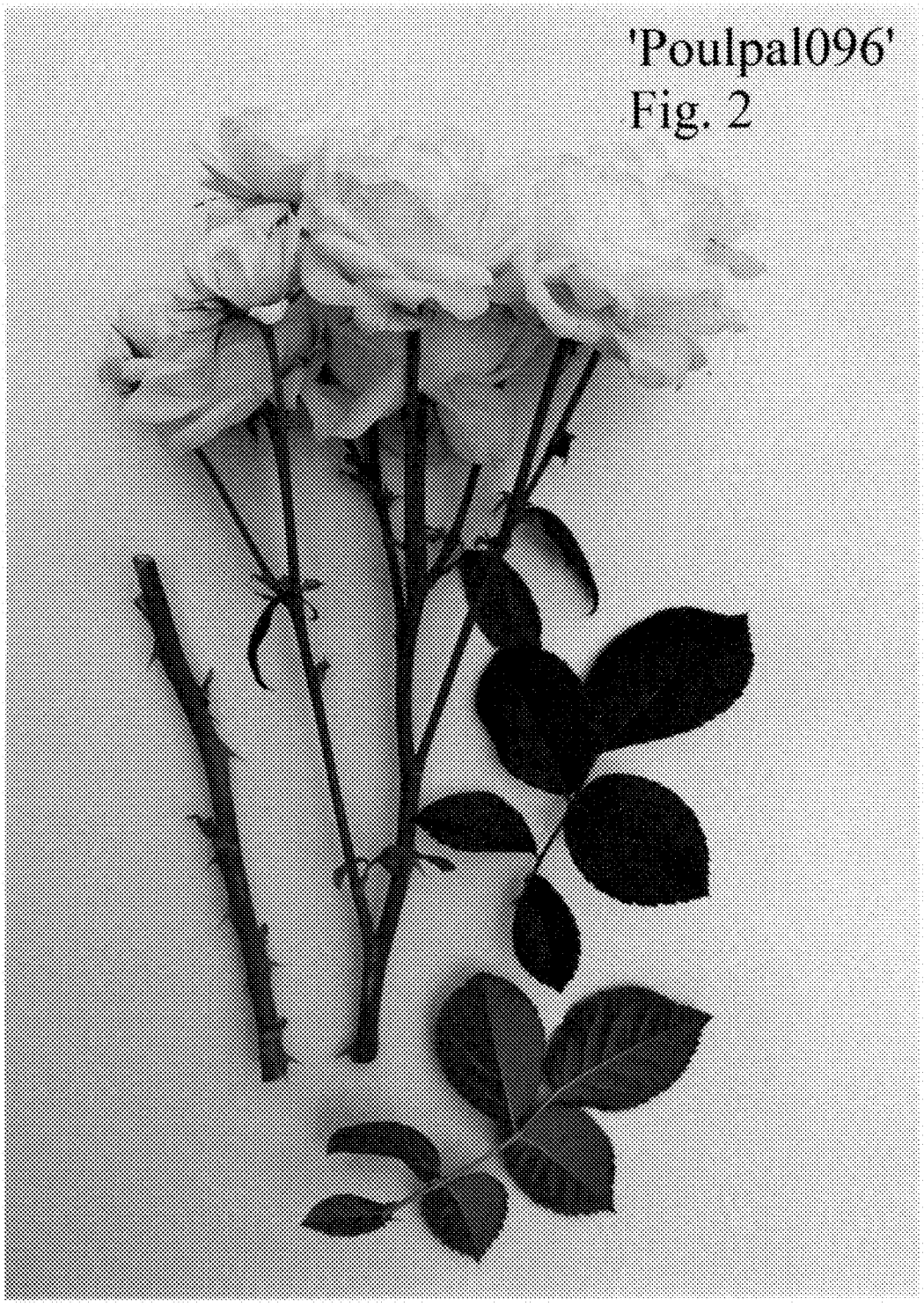

Specifically illustrated in FIG. 2 of the drawings is a cluster of flowers on a branch, bare stem, and mature leaves.

Plants shown are 2 years of age.

DETAILED DESCRIPTION OF THE VARIETY

The following is a description of 'Poulpa1096', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpa1082', U.S. Plant Pat. No. 32,927 are compared to 'Poulpa1096'. For the claimed plant newly opened flowers are White Group 155 A with intonations of Orange-White Group 159A. After flowers are mature general tonality becomes White Group 155A. For the comparison variety, the general tonality of flower colour is Yellow Group 11D with intonations of Yellow-Orange Group 14D. The comparison variety has 65 flower petals, while the new variety has 80 petals. The comparison variety has a moderate floral scent, while the new variety has strong flower perfume.

Flower and Flower Bud

Blooming habit: Continuous.

Flower bud:

- *Size.*—Upon opening, 17 mm in length from base of receptacle to end of bud. Bud diameter is 11 mm.
- *Bud form.*—Globose.
- *Bud color.*—As sepals divide petals are White Group 155B.
- *Sepal inner surface.*—Color: Yellow-Green Group 146A, with intonations of Greyed-Red Group 178A. Surface: Lightly pubescent.
- *Sepal outer surface.*—Color: Yellow-Green Group 146A. Texture: Smooth.
- *Sepal shape.*—Apex: Cirrhose. Base: Flat at union with receptacle.
- *Sepal margin.*—Margins have moderate foliaceous appendages on three of the five sepals.
- *Sepal size.*—31 mm long, 15 mm wide.
- *Receptacle.*—Texture: Smooth. Size: 5 mm in height, 7 mm wide. Color: Yellow-Green Group 144A. Shape: Funnel.
- *Pedicel.*—Surface: Smooth. Length: About 70 mm. Diameter: 3 mm on average. Color: Yellow-Green Group 144A. Strength: Strong.
- *Peduncle.*—Length: 35 to 80 cm. Diameter: About 3 mm. Color: Yellow-Green Group 144A. Texture: Smooth.

Flower bud development: Flower buds are borne in clusters of about 5 flowers per stem in the panicle form.

Flower bloom:

- *Fragrance.*—Strong perfume.
- *Duration.*—The blooms have a duration on the plant of approximately 19 days. Petals fall cleanly away from plant after flowers have fully matured.
- *Size.*—Flower diameter is 85 mm when open. Flower depth is 45 mm.
- *Flower shape.*—Globose cup, very double flower, with petals that curve out from the center.
- *Shape of flower, side view.*—The upper portion is convex. The lower portion is flat concave.

Petalage: Under normal conditions, flowers have about 80 petals.

General tonality of flower: Newly opened flowers are White Group 155 A with intonations of Orange-White Group 159A. After mature tonality changes to White Group 155A.

Petal color:

- *Upon opening, outer petals.*—Upper surface: White Group 155C. Lower surface: White Group 155C.
- *Upon opening, inner petals.*—Upper surface: White Group 155B with intonations of Yellow-White Group 158B. Lower surface: White Group 155B with intonations of Yellow-White Group 158C.
- *Basal petal spots, upon opening.*—Upper surface: Green Yellow Group 1D. Lower surface: Green Yellow Group 1D.
- *After opening, outer petals.*—Upper surface: White Group 155C. Lower surface: White Group 155C.
- *After opening, inner petals.*—Upper surface: White Group 155C. Lower surface: White Group 155C.
- *Basal petal spots.*—After opening no distinctive coloration at the petal base observed.

Petals:

- *Petal reflex.*—Strong bilateral reflex.
- *Margin.*—Entire and uniform. Light undulations.
- *Shape.*—Broad and elliptic. Apex shape: Rounded. Base shape: Acute.
- *Size.*—45 mm (l)×35 mm (w).
- *Texture.*—Smooth.
- *Thickness.*—Average.

Petaloids:

- *Size.*—20 mm (l) by 11 mm (w).
- *Quantity.*—About 10.
- *Shape.*—Elliptical with an acute base and apex.
- *Color.*—White Group 155B with other intonations of Yellow-Green Group 150D.

Reproductive flower parts:

- *Pollen.*—None observed.
- *Anthers.*—Size: 3 mm in length. Color: Yellow-White Group 158A. Quantity: 40 on average.
- *Filaments.*—Color: Green-White Group 157A. Length: 6 mm.
- *Pistils.*—Length: 12 mm. Quantity: 35 on average.
- *Stigmas.*—Color: Green-White Group 157A.
- *Styles.*—Color: Green-White Group 157A.
- *Location of stigmas.*—Superior in location relative to the length of the filaments and the height of the anthers.
- *Hips.*—None Observed.

Plant

Plant growth: Upright. Plants are about 60 cm in height, and 35 cm wide.

Stems:

- *Color of juvenile growth.*—Yellow-Green Group 144B.
- *Color of mature growth.*—Yellow-Green Group 144A.
- *Length.*—Canes are about 35 cm from the base of the plant to the flowering portion.
- *Diameter.*—About 6 mm.
- *Internodes.*—On mature canes about 42 mm between nodes.
- *Surface texture.*—Young wood: Smooth. Older wood: Smooth.

Long prickles:

- *Incidence.*—8 prickles per 10 cm of stem.
- *Size.*—Average length of prickles on mature stems is 10 mm.
- *Shape.*—Upper portion is linear. Lower portion is concave.

*Color.*—Juvenile prickles: Greyed-Yellow Group 160C. Mature prickles: Greyed-Yellow Group 160C with intonations of Greyed-Orange Group 170D.

Plant foliage:

*Compound leaf.*—122 mm (l)×113 (w).

*Quantity.*—2 leaves per 10 cm of stem on average.

*Leaf bearing angle to the stem.*—45 degrees.

*Color of juvenile foliage.*—Upper side: Yellow-Green Group 144A with intonations of Greyed-Orange Group 165A at the margins. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 11 mm long, 2 mm wide. Quantity: 2 per compound leaf. Shape: Linear, slightly broad based with outward extending apices. Margins: Finely serrated. Color:

*Petiole.*—Length: 15 mm. Diameter: 2 mm. Upper surface color: Yellow-Green Group 144A. Lower surface color: Yellow-Green Group 144B.

*Rachis.*—Length: 37 mm. Upper surface color: Yellow-Green Group 144A. Lower surface color: Yellow-Green Group 144B.

*Leaflet.*—Quantity: Normally 5 leaflets. Margins: Serrated. Size: Terminal leaflets are about 71 mm long, 47 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in The American Horticulture Society heat zone 7.

I claim:

1. A new and distinct variety of rose plant named 'Poulpa1096' substantially as described and illustrated herein.

* * * * *

'Poulpal096'

'Poulpal096'